(12) United States Patent
Eason et al.

(10) Patent No.: US 6,948,496 B2
(45) Date of Patent: Sep. 27, 2005

(54) INHALERS

(75) Inventors: Stephen William Eason, Norfolk (GB); Quentin John Harmer, Cambridge (GB); Matthew Neil Sarkar, Cambridge (GB)

(73) Assignee: Vectura, Limited, Wilshire (GB)

( * ) Notice: Subject to any disclaimer, the term of this patent is extended or adjusted under 35 U.S.C. 154(b) by 125 days.

(21) Appl. No.: 10/333,524

(22) PCT Filed: Jul. 20, 2001

(86) PCT No.: PCT/EP01/08416
§ 371 (c)(1),
(2), (4) Date: May 13, 2003

(87) PCT Pub. No.: WO02/07805
PCT Pub. Date: Jan. 31, 2002

(65) Prior Publication Data
US 2003/0172926 A1 Sep. 18, 2003

(51) Int. Cl.⁷ ............................................. A61M 15/00
(52) U.S. Cl. .......................... 128/203.15; 128/203.12; 128/203.21
(58) Field of Search ...................... 128/203.12, 203.15, 128/203.21; 604/58

(56) References Cited

U.S. PATENT DOCUMENTS

| | | | | |
|---|---|---|---|---|
| 16,066 A | * | 11/1856 | Murphy ................. | 128/203.15 |
| 3,362,405 A | * | 1/1968 | Hazel ..................... | 128/203.15 |
| 3,949,751 A | | 4/1976 | Birch et al. | |
| 4,064,878 A | | 12/1977 | Lundquist ................... | 128/206 |
| 4,069,819 A | | 1/1978 | Valentini et al. ............ | 128/206 |
| 4,143,658 A | * | 3/1979 | Rambosek et al. ..... | 128/203.15 |
| 4,338,931 A | | 7/1982 | Cavazza ................ | 128/203.15 |
| 4,534,343 A | * | 8/1985 | Nowacki et al. ....... | 128/200.23 |
| 4,570,630 A | * | 2/1986 | Elliott et al. ........... | 128/203.15 |
| 5,161,524 A | * | 11/1992 | Evans ................... | 128/203.15 |
| 5,186,164 A | * | 2/1993 | Raghuprasad .......... | 128/200.14 |
| 5,263,475 A | * | 11/1993 | Altermatt et al. ....... | 128/203.15 |
| 5,320,714 A | * | 6/1994 | Brendel ................. | 128/203.15 |
| 5,349,947 A | * | 9/1994 | Newhouse et al. ..... | 128/203.21 |
| 5,476,093 A | * | 12/1995 | Lankinen ............... | 128/203.15 |
| 5,596,982 A | * | 1/1997 | Blaha-Schnabel ...... | 128/200.14 |
| 5,692,496 A | * | 12/1997 | Casper et al. .......... | 128/203.15 |
| 5,755,221 A | * | 5/1998 | Bisgaard ................ | 128/203.15 |
| 5,785,049 A | | 7/1998 | Smith et al. ........... | 128/203.15 |
| 5,823,183 A | * | 10/1998 | Casper et al. .......... | 128/203.15 |
| 5,875,776 A | * | 3/1999 | Vaghefi ................. | 128/203.15 |
| 5,896,855 A | * | 4/1999 | Hobbs et al. ........... | 128/203.15 |
| 5,988,163 A | * | 11/1999 | Casper et al. .......... | 128/203.15 |
| 6,109,261 A | * | 8/2000 | Clarke et al. .......... | 128/203.15 |
| 6,347,629 B1 | * | 2/2002 | Braithwaite ............ | 128/203.15 |
| 6,595,210 B2 | * | 7/2003 | Ohki et al. ............. | 128/203.15 |

FOREIGN PATENT DOCUMENTS

| | | |
|---|---|---|
| EP | 0525720 A1 | 2/1993 |
| EP | 0940154 A2 | 9/1999 |
| FR | 2352556 | 12/1977 |
| WO | 9503846 | 2/1995 |
| WO | 9826827 | 6/1998 |
| WO | 9912597 | 3/1999 |

* cited by examiner

*Primary Examiner*—Aaron J. Lewis
(74) *Attorney, Agent, or Firm*—Davidson, Davidson & Kappel, LLC

(57) ABSTRACT

An inhaler for producing an inhalable aerosol of a powdered medicament comprises a cyclone (1) with a tangential air inlet (3) and an axial air outlet (4). The cyclone (1) aerosolises and retains an aerosol of powdered medicament in an airflow circulating between the inlet (3) and the outlet (4). The cyclone (1) has an exit port (2) which is open to atmosphere. When the aerosol is to be inhaled, the pressure in the cyclone (1) is increased by increasing the airflow to the inlet (3) which causes the aerosol to discharge through the exit port (2). The inhaler has the advantage that the rate of discharge of the aerosol can be controlled independently of the rate of airflow required to aerosolise the medicament.

11 Claims, 3 Drawing Sheets

INHALERS

The present invention relates to inhalers and in particular inhalers for the delivery of a medicament to the lung, more particularly a medicament in powder form.

In recent times, there has been a growing interest in the systemic delivery of pharmaceutically-active medicaments via the lung. Such a method of delivery is generally more attractive to the patient than methods such as injection, because it does not involve a needle and can be carried out discreetly in public.

In the case of medicaments in liquid form, the provision of an inhalable aerosol of the medicament can be achieved with a nebuliser or the like. A known device for liquid aerosol creation in a nebuliser is a so-called "cyclone". The cyclone comprises a cylindrical chamber with an axial outlet and a tangential inlet.

For a medicament in a particulate form the provision of an inhalable aerosol is more difficult than for a liquid, because it is necessary to achieve a large repeatable dose of fine particles. In order for the particles of medicament to reach the lung and thus be absorbed into the bloodstream, the particles must have an effective diameter in the range of approximately 1 to 5 microns. If the particles are larger than 5 microns they may not be transported by the inhaled airflow deep into the lung, because they are likely to be trapped in the respiratory passages before reaching the deep lung. For example, particles of the order of 10 microns are unlikely to progress further than the trachea and particles of the order of 50 microns tend to deposit on the back of the throat when inhaled. Furthermore, if the particles are less than 1 micron in effective diameter, the particles may not be absorbed in the lung, because they are small enough to be expelled from the lung with the exhaled airflow.

Thus, it will be seen that it is important that the powdered medicament is delivered with an accurately controlled range of particle size in order that it is absorbed effectively in the lung.

It is known for the powdered medicament to be mixed with an excipient (an inert substance, such as lactose, which is combined with the medicament to prepare a convenient dosage form) of relatively large particle size, for example 50 to 100 microns, to improve the handling properties of the medicament. The medicament attaches electrostatically to the surface of the excipient. In some cases, the particles of medicament agglomerate to form particles of a larger effective diameter. In either case, it is necessary to separate the medicament particles from the excipient and from each other in order to provide an inhalable aerosol which will deliver the medicament for absorption through the lung.

The particles can be separated by generating shear forces between the particles, for example by providing a substantial velocity gradient across the particles. This may be done, for example, by forcing the powder through a narrow nozzle at high speed or introducing the powder into a turbulent air stream.

In traditional metered dose inhalers (MDIs) it is common for the emitted dose (the amount of medicament that enters the patient's airway) to be around 80 to 90% of the dose ejected from the inhaler. The respirable dose (the amount of medicament that reaches the lung) may be only around 50% of the emitted dose. However, the variation in the respirable dose of known inhalers can be ±20 to 30%. Such variation may be acceptable in the case of asthma drugs and the like, but when the medicament is a more potent drug such as insulin, growth hormone or morphine, this amount of variability in the dosing is unacceptable. The relatively low respirable dose also represents a significant wastage of what may be an expensive drug. Furthermore, there may be side effects if the proportion of the emitted dose which is not respired is swallowed.

Thus, it is important for the systemic delivery of medicaments by inhalation that a repeatable dose of fine particles can be produced.

It is known for so-called "spacers" to be used in the generation of the aerosol from a metered dose inhaler. The spacer fits onto the mouthpiece of the inhaler and comprises a chamber into which the dose of medicament is ejected by the inhaler. The patient is then able to inhale the dose from the spacer through a corresponding mouthpiece on the spacer.

Large volume spacers are used where the patient is unable to inhale at the same time as operating the metered dose inhaler due to a lack of coordination. Small volume spacers are used to trap large particles which would stick to the back of the throat and may cause undesirable side-effects.

Such spacers retain a fast-moving aerosol ejected from the inhaler, and hold it until it can be inhaled by the user. However, a proportion of the particles in the aerosol will be retained on the walls of the spacer which makes it difficult to predict reliably the dose of medicament that the user inhales. Furthermore, the larger size of the spacer makes the inhaler more cumbersome and less discreet.

The present invention, at least in its preferred embodiments, seeks to provide an inhaler for reliably generating an inhalable aerosol of a powdered medicament with an effective particle size that is sufficiently small for the medicament to be delivered to and absorbed in the lungs of a patient.

Viewed from a first aspect, the invention provides an inhaler for producing an inhalable aerosol of a powdered medicament, the inhaler comprising:

an aerosolising device having an exit port and being arranged to retain, in use, an aerosol of a powdered medicament in a circulating airflow; and discharge means arranged to control the discharge of the aerosol through the exit port.

According to the invention, the aerosol of powdered medicament and air is retained in the aerosolising device which deagglomerates the particles of medicament to provide an aerosol of sufficiently small particles for delivery of the medicament to the lung. The aerosol may circulate in the aerosolising device until it is required by the user, at which time the discharge means controls the exit of the aerosol from the aerosolising device, so that it can be inhaled by the user.

By means of the inhaler according to the invention, the aerosol can be generated in a fast-moving circulating airflow in the aerosolising device to provide the necessary shear forces for the required degree of deagglomeration of the powdered medicament. However, the rate at which the aerosol is discharged from the aerosolising device can be controlled by the discharge means, independently of the speed of the circulating airflow.

Thus, with the inhaler according to the invention, a slow-moving aerosol can be generated for inhalation by the user. Moreover, the aerosol retained by the aerosolising device can be inhaled by the user over multiple inspirations, as it is not necessary for all of the aerosol to be discharged in one go. This may be much easier for the user than attempting to inhale the whole of a fast-moving aerosol at once. Furthermore, the rate of discharge of the aerosol can be carefully controlled so that the medicament particles in the slow-moving aerosol are less likely to be deposited on the walls of the inhaler mouthpiece rather than inhaled by the user.

The discharge means may operate in any suitable manner. For example, the discharge means may comprise an electrical device arranged to electrostatically expel the aerosol from the aerosolising device. Alternatively, the discharge means may be arranged to expel the aerosol mechanically from the aerosolising device. For example, the aerosol may be subject to a centrifugal force in the aerosolising device and the discharge means may be arranged to open the exit port so that the aerosol is ejected by virtue of its own momentum.

In a preferred embodiment, the discharge means is arranged to provide a pressure differential across the exit port.

The discharge means may comprise a cover, closure or valve for the exit port which is opened to discharge the aerosol. In this case, the interior of the aerosolising device may be at higher than atmospheric pressure when the exit port is opened. The interior of the aerosolising device may be maintained at higher than atmospheric pressure.

In a preferred arrangement, the exit port is open to atmosphere, in use. In this case, the discharge means controls a pressure differential across the exit port in order to retain or discharge the aerosol. This has the advantage that the discharge of the aerosol can be controlled by pressure alone without any mechanical closure of the exit port so that there are fewer moving parts in the inhaler. In addition, the rate of discharge of the aerosol can be varied.

In order to retain the aerosol in the aerosolising device, the pressure within the aerosolising device may be maintained approximately equal to that on the side of the exit port remote from the aerosolising device. This can be achieved, when the exit port is open to atmosphere, by ensuring that there is no net inflow of air into the aerosolising device. In one arrangement, the aerosolising device has an inlet and an outlet and air is circulated by a pump from the outlet to the inlet in a recirculation loop. The recirculation loop is closed while the aerosol is retained in the aerosolising device, which ensures that the flow into the inlet is equal to the flow out of the outlet, so that there is no net inflow into the aerosolising device.

In order to discharge the -aerosol, the discharge means may be arranged to increase the pressure in the aerosolising device. In this case the pressure in the aerosolising device becomes greater than that on the other side of the exit port and the aerosol is forced out of the aerosolising device. The pressure in the aerosolising device may be increased by reducing the volume of the aerosolising device, for example by means of a piston or bladder or by deformation of one or more walls of the device. Alternatively, the discharge means may be arranged to increase the airflow into the aerosolising device. For example, an inlet port in the aerosolising device or in the recirculation loop may be opened to allow an inflow of air into the aerosolising device.

In an alternative arrangement, the discharge means may be arranged to reduce the pressure on the side of the exit port remote from the aerosolising device, in order to the discharge the aerosol. For example, the aerosol may be drawn out of the aerosolising device into a further chamber by means of a piston, bladder, pump or the like. In a particularly advantageous arrangement, the discharge means comprises a mouthpiece and inhalation by a user on the mouthpiece reduces the pressure on the side of the exit port remote from the aerosolising device to discharge the aerosol. In this case, the pressure differential across the exit port is created by the inspiration of the user so that discharge of the aerosol coincides exactly with inhalation.

The aerosolising device may comprise any suitable device which is arranged to deagglomerate the powdered medicament and form an aerosol therefrom. In a preferred embodiment, the aerosolising device comprises a cyclone having a tangential inlet and an axial outlet. In this case, the aerosol of medicament spins in the cyclone until the aerosol is discharged.

In general, the cyclone is configured as a substantially cylindrical cavity provided with a tangential inlet and an axial outlet. The diameter of the cyclone may be between about 2 and 15 mm, preferably between 3 and 10 mm, most preferably about 6 mm. The height of the cyclone chamber may be between 1 and 10 mm, preferably between 2 and 7 mm, preferably about 3 mm. The outlet of the cyclone may project into the interior of the cyclone. This reduces the chance of particles of circulating medicament escaping from the cyclone through the outlet.

It is desirable for the cyclone to generate as much shear as possible within the airflow. At small radii, close to the axis of the cyclone, the high angular velocities increase the effective viscosity of the air and can cause a central cylindrical region lying along the axis to rotate as a rigid body within which the shear forces are minimal. Thus, according to an advantageous arrangement, the cyclone is provided with an axial member for directing the medicament towards the walls of the cyclone. In this way, the aerosol is unable to enter the very central zone of the cyclone where the shear forces are at a minimum. Alternatively or in addition, the outlet of the cyclone may be annular to encourage the airflow away from the central axial region of the cyclone.

The exit port may be formed simply as an aperture in the aerosolising device. The aerosolising device may comprise a plurality of exit ports. The exit port(s) may comprise a plurality of apertures. Multiple ports or apertures have the advantage that the total area of the exit port(s) can be maximised without unduly disturbing the airflow within the aerosolising device.

Where the aerosolising device has an axis of rotation of the aerosol the location of the exit port(s) is preferably spaced from the axis. This ensures that the fully aerosolised aerosol is ejected from the exit port(s). Furthermore, the exit port(s) is preferably located opposite the air outlet of the aerosolising device. In this case, the construction of the inhaler is simplified and the possibility of medicament being accidentally ejected from the exit port during aerosolisation is reduced.

The inhaler may comprise a drug dosing device arranged to release a dose of the powdered medicament into the circulating airflow. The powdered medicament may be entrained in the airflow to the aerosolising device.

In a preferred embodiment, the drug dosing device comprises a chamber arranged to receive a capsule of a medicament and a piercing device comprising a needle arranged to pass right through the capsule to form an entry hole and an exit hole therein, so that, in use, an airflow can pass through the capsule to entrain the medicament. In such an arrangement, the capsule forms a conduit for the airflow so that the medicament can be entrained directly from the capsule in the airflow.

This in itself is believed to be a novel feature and thus, viewed from a second aspect, the invention provides a drug dosing device, in particular for an inhaler, comprising:

a chamber arranged to receive a capsule of a medicament; and a piercing device comprising a needle arranged to pass right through the capsule to form an entry hole and an exit hole therein, so that, in use, an airflow can pass through the capsule to entrain the medicament.

The capsule may be any suitable container for the medicament, in particular a gelatine capsule or a foil blister.

Advantageously, the needle is hollow and forms a conduit for the airflow. In this way, once the needle has pierced the capsule to form the entry hole the airflow can be supplied to the capsule via the needle.

In a preferred arrangement, the needle is arranged to form a temporary bypass for the airflow between the entry hole and the exit hole.

As the needle is arranged to pass right through the capsule, the withdrawal of the needle may advantageously control the rate of entrainment of the medicament in the airflow. As the needle is withdrawn, more of the medicament is located between the exit port and the end of the needle and is entrained in the airflow from the end of the needle. Such an arrangement provides a particularly convenient means of controlling the gradual release of the medicament into the airflow.

Alternatively, the medicament may be sucked through the needle by an airflow into the needle.

Some embodiments of the invention will now be described by way of example only and with reference to the accompanying drawings, in which.

In the various embodiments of the invention, corresponding components are given corresponding reference numerals. In the second and third embodiments of the invention, components which are not specifically described have previously been described in relation to the first embodiment.

Figure 1:
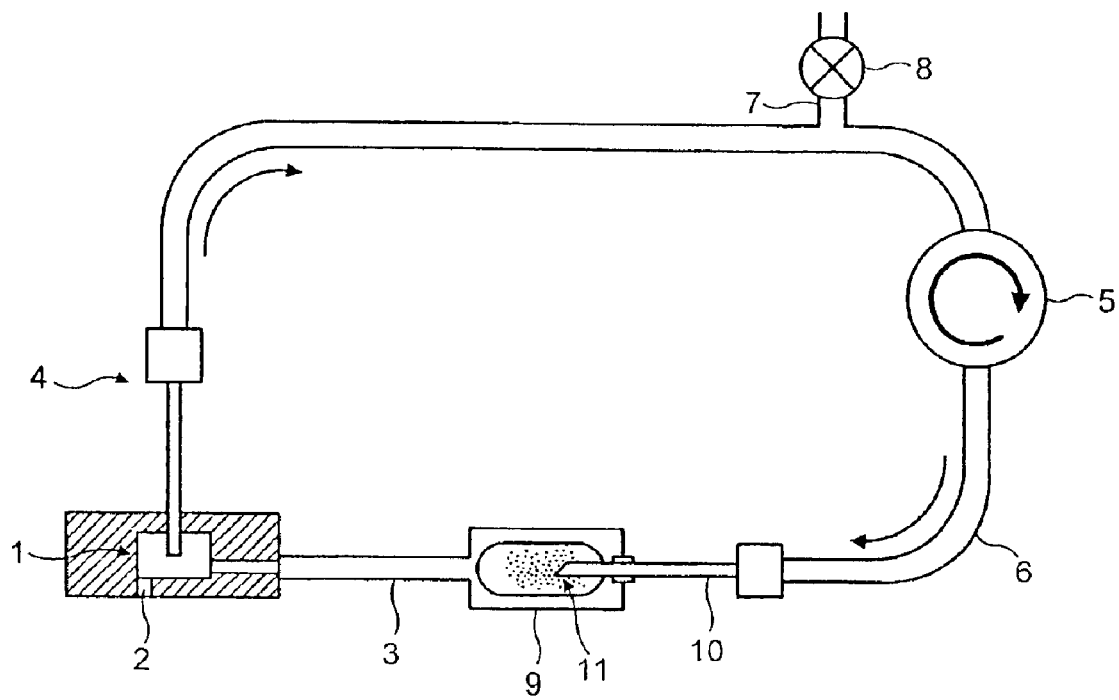
FIG. 1 shows a schematic arrangement of an inhaler according to a first embodiment of the invention.

FIG. 1 shows schematically a prototype test rig for an inhaler according to an embodiment of the invention. The test rig aerosolises a drug in dry powder form to make it available for inhalation. A particular feature of the apparatus is the ability to create a slow-moving powder aerosol cloud in a controlled manner.

As shown in FIG. 1, apparatus according to a first embodiment of the invention comprises an aerosolising device in the form of a cyclone chamber 1 having a drug exit port (or nozzle) 2, a tangential air inlet 3 and an axial air outlet 4. The cyclone 1 is in the form of a cylindrical chamber having an internal diameter of about 4 mm and an internal height of about 3 mm. Each of the exit port 2, inlet 3 and outlet 4 have an internal diameter of 0.3 mm.

Figure 2:
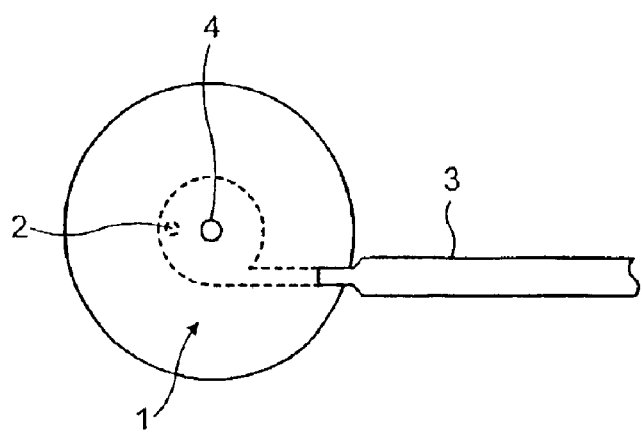
FIG. 2 is a plan view of an aerosolising device of the embodiment of FIG. 1.

FIG. 2 is a plan view of the cyclone 1, which shows that the inlet 3 is substantially tangential to the wall of the cyclone 1 and the outlet 4 is concentric with the axis of the cyclone 1. The exit port 2 is located on the opposite face of the cyclone 1 to the axial inlet 4 and is offset from the axis of the cyclone 1. The length of the exit port 2 is as short as possible to reduce the possibility of deposition of the drug on the walls of the exit port 2. In the embodiment shown, the cyclone 1 is machined from acrylic, although a wide range of alternative materials is possible.

The apparatus shown in FIG. 1 further comprises a pump 5 which is arranged to circulate air from the outlet 4 of the cyclone 1 to the inlet 3 via tubing 6. In the embodiment shown, the pump 5 is a Sensidyne "Dual Head C" micro-air pump available from Sensidyne, Inc. of Clearwater, Fla., USA, powered from a 12 V power supply (not shown). The pump 5 is of a type that generates suction and positive pressure through respective inlet and outlet ports.

Between the cyclone outlet 4 and the pump 5, there is provided an air inlet port 7 which is normally closed by a valve 8. When the valve 8 is closed, the entire system is only open to atmosphere at the exit port 2 in the bottom surface of the cyclone chamber 1. Since there are no other vents to atmosphere there is no net flow through the exit port 2 when the pump 5 is running at a constant rate. Furthermore, the pressure in the cyclone chamber 1 in the region of the exit port 2 is atmospheric pressure, assuming that the system is operating in free air, because there is no flow through, and therefore no pressure differential across, the exit port 2. In this way, the system can be thought of as self-balancing, because independently of the characteristics of the pump 5 and the pressure drop in the various components, such as the capsule chamber 9 and cyclone inlet 3, the pressure in the cyclone chamber 1 is atmospheric, with no flow through the exit port 2.

When the valve 8 is opened, the self-balancing characteristic of the system is changed. Air is sucked into the system through the open air inlet port 7 where the pressure is below atmospheric and a corresponding volume of air is blown out of the exit port 2 of the cyclone chamber 1. The air inlet port 7 and associated valve 8 therefore provide a means of controlling the discharge of air (and the aerosol) from the cyclone chamber 1.

If the air inlet port 7 were located downstream of the pump 5 where the pressure is above atmospheric, air would be blown out of the air inlet port 7 when the valve 8 is opened and a corresponding volume of air would be drawn in through the exit port 2 in the cyclone chamber 1.

As shown in FIG. 1, the apparatus comprises a drug dosing device in the form of a capsule chamber 9 which receives a hollow needle 10 for piercing a capsule 11 of powdered medicament. The capsule 11 is typically a standard gelatin capsule, such as a Shionogi Qualicap available from Shionogi & Co. Ltd. of Osaka, Japan, containing between 3 and 5 mg of powdered drug. The capsule chamber 9 is located between the pump 5 and the inlet 3 of the cyclone 1. The air flow from the pump 5 is directed through the interior of the hollow needle 10 into the capsule chamber 9 and from the capsule chamber 9 to the inlet 3 of the cyclone 1. The needle 10 is sufficiently long that when it is inserted right into the capsule chamber 9, it passes right through the capsule 11 located therein, piercing both ends of the capsule 11, and connects the airflow from the pump 5 directly to the inlet 3 of the cyclone 1, bypassing the interior of the capsule chamber 9.

In operation of the prototype inhaler of FIG. 1, a drug capsule 11 is first placed in the capsule chamber 9, with the needle 10 withdrawn from the capsule chamber 9. The capsule 11 is then pierced by pushing the needle 10 right through both ends of the capsule 11 such that it projects from the end of the capsule chamber 9 closest to the cyclone chamber 1 into the inlet 3 of the cyclone 1.

With the valve 8 closed, the circulating pump 5 is switched on to blow air into the cyclone chamber 1 through the tangential inlet 3 and suck air from the axial outlet 4. The airflow is directed by the internal surface of the cyclone chamber 1 in a roughly helical path from the inlet 3 towards the outlet 4. The flow rate through the cyclone 1 is in the region of 2 to 4 litres per minute using the Sensidyne "Dual Head C" micro-air pump. Computer modelling of the flow in the cyclone chamber 1 indicates that such a rate of flow creates a swirling flow of around 150,000 rpm within the cyclone chamber 1.

The powdered drug is introduced into the cyclone chamber 1 by drawing the needle 10 back through the capsule 11, so that the airflow from the open end of the needle 10 blows the powdered drug through the capsule 11 and out of the hole made by the needle 10 in the end of the capsule 11 proximate the inlet 3 of the cyclone 1. Withdrawal of the needle 10 creates an airflow in the capsule 11, causing the drug to be entrained and swept into the cyclone chamber 1. The valve 8 remains closed, to ensure that the drug remains in the cyclone 1.

The rapid rotation of the air and entrained drug in the cyclone 1 has two effects. Firstly, a combination of high-shear flow and impact against the walls of the cyclone 1 causes the drug to be deagglomerated, i.e. any clumps of particles are broken down such that the drug powder becomes finely divided. Secondly, the centrifugal force experienced by the circulating particles acts against the airflow out of the outlet 4 of the cyclone 1 to prevent the particles being drawn by the airflow out of the cyclone 1. In this way an aerosol of finely-divided particle of the drug is formed and retained in the cyclone 1.

When it is required to discharge the aerosol, the valve 8 is opened, so that the mixture of particles and air is caused to flow through the exit port 2. This results in a slow-moving aerosol cloud which can be inhaled, for example through a mouthpiece (not shown). The aerosol is ideal for inhalation, because it is both finely divided and slow-moving. These two factors increase significantly the proportion of the drug that is conveyed to either the small airways of the lung or the alveoli.

Figure 3:
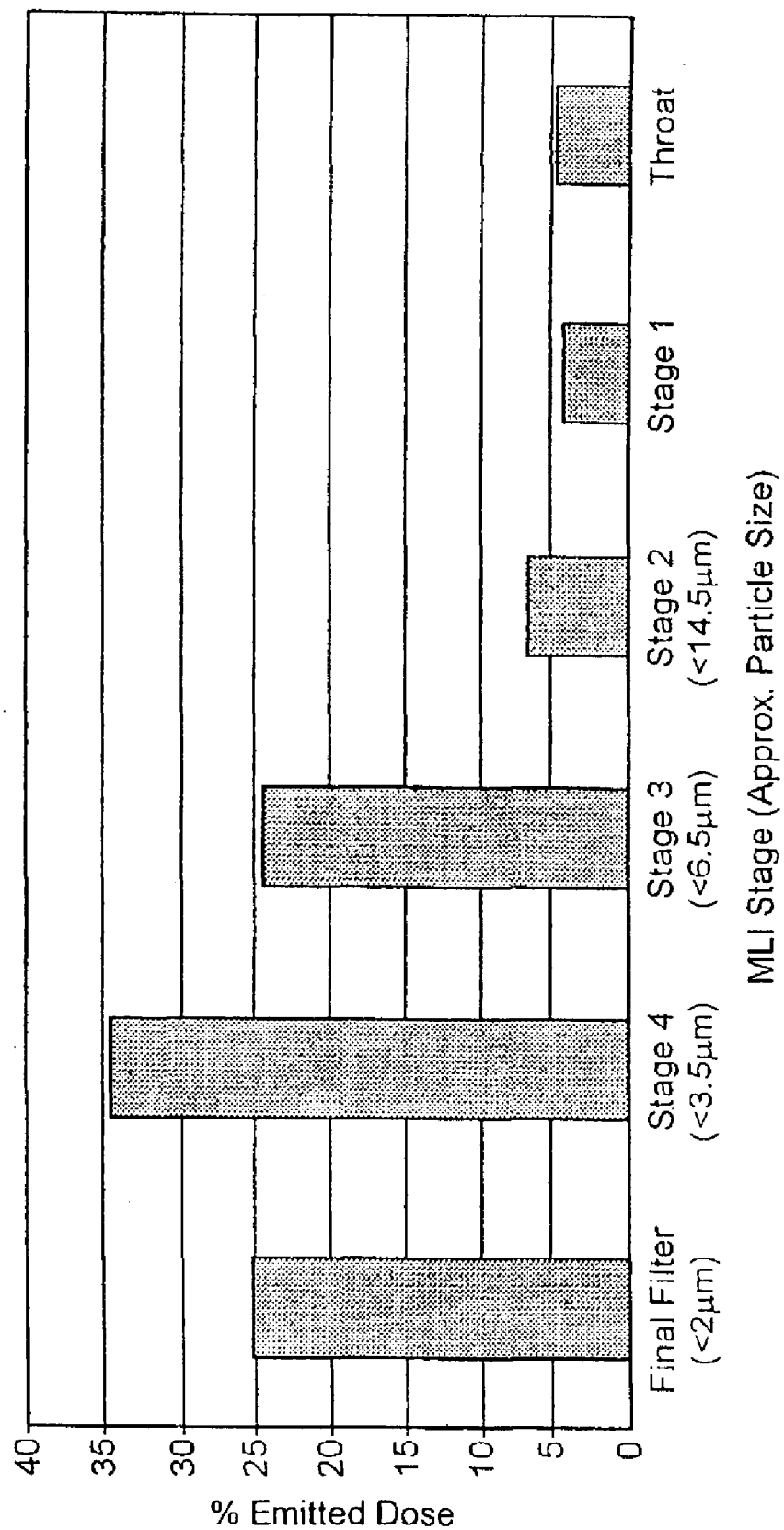
FIG. 3 shows the results of a multi-stage liquid impinger test of the embodiment of FIG. 1.

FIG. 3 shows the results obtained using an Astra Draco Multi-Stage (4/5) Liquid Impinger (MLI), available from Draco Lakemedel AB of Lund, Sweden, to assess the percentages of the emitted dose of the drug which would be expected to reach successively deeper stages of the lung. A Multi-Stage Liquid Impinger is commonly used to assess the performance of inhaler devices. The drug used in the testing was sodium cromoglycate.

The results in FIG. 3 show that almost 85% of the drug emitted is delivered to either stage 3, stage 4 or the final filter of the MLI apparatus. This indicates that these particles are highly likely to be delivered to the lower airways and alveoli of the patient's lung in practice.

A significant advantage of the inhaler according to the invention is that the process of deagglomeration is independent of the process of ejection into the inspiratory flow. Most powder inhalers deagglomerate the drug as part of the ejection process which means that the rate of ejection is determined by the flow rate required for effective deagglomeration. The degree of control over the timing and velocity of the drug aerosol is therefore very limited with such known devices.

Figure 4:
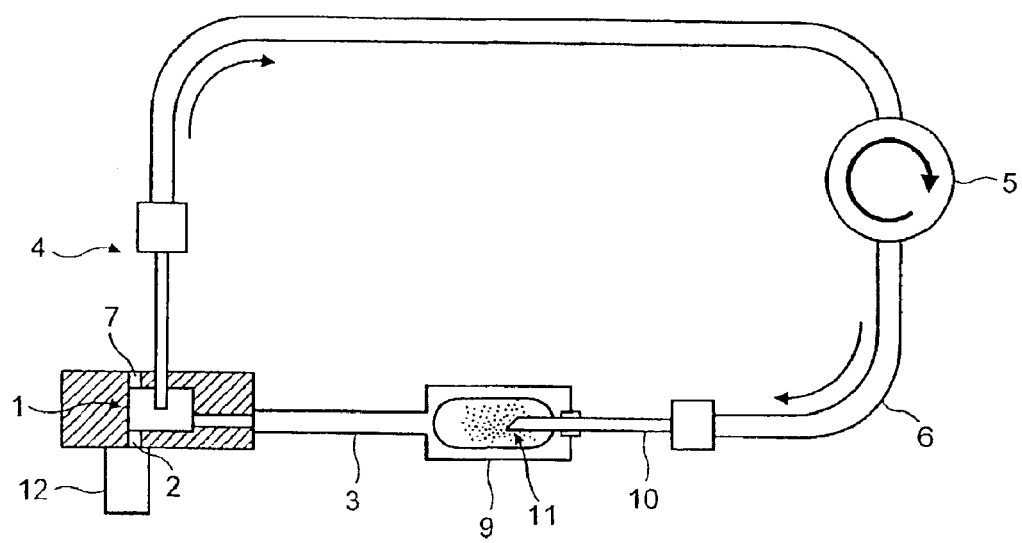
FIG. 4 shows a schematic arrangement of an inhaler according to a second embodiment of the invention.

FIG. 4 shows a schematic arrangement of an inhaler according to a second embodiment of the invention. This embodiment differs from the embodiment of FIG. 1 in that the air inlet port 7 is provided in the top of the cyclone chamber 1 and there is no valve 8.

According to the second embodiment of the invention, inhalation by the patient produces the necessary pressure drop to discharge the drug aerosol. The exit port 2 is connected directly to a mouthpiece 12, such that inhalation through the mouthpiece 12 draws the drug into the inspiratory flow. The air inlet port 7 is positioned symmetrically to the exit port 2 and allows a flow of air into the cyclone 1 to replace the air that has been inhaled.

Figure 5:
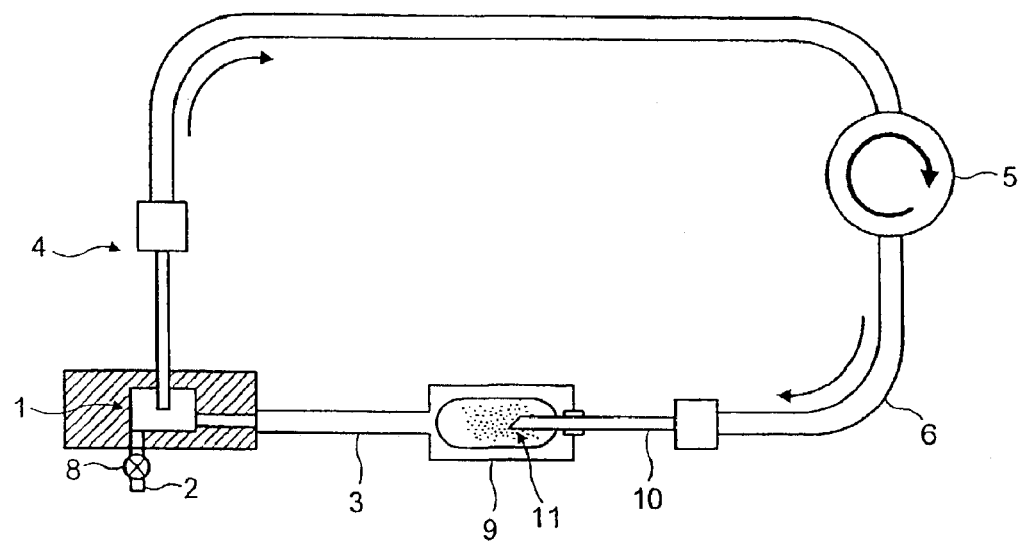
FIG. 5 shows a schematic arrangement of an inhaler according to a third embodiment of the invention.

FIG. 5 shows a schematic arrangement of an inhaler according to a third embodiment of the invention. This embodiment differs from the previous embodiments in that there is no air inlet port 7. In this embodiment, the normally-closed valve 8 shuts off the exit port 2 to retain the aerosol in the cyclone 1. The inhaler is operated with a permanent slight over-pressure in the cyclone 1, and the mechanically operated valve 8 is used to retain the aerosolised drug in the cyclone until the desired moment of release.

Further variations to the described embodiments are also within the scope of the invention. For example, although a continuous electrical pump has been described, alternatives such as spring-powered piston pumps or air-pumps using eductors may also be, used. Furthermore, the described drug dosing device may be replaced, for example by a multiple-dose cartridge or a powder reservoir system. The point at which the drug is introduced into the circulating system may also be changed. For example, the drug may be introduced directly into the cyclone chamber rather than into the cyclone inlet.

Although the aerosol of medicament has been described herein as an aerosol of powdered medicament in air, the medicament may be dispersed in any other gas or mixture of gases, as required. Furthermore, although the invention has been described in terms of apparatus, the invention also extends to a method of generating an inhalable aerosol of a powdered medicament and/or a method of drug dosing as described herein.

In summary, an inhaler for producing an inhalable aerosol of a powdered medicament comprises a cyclone with a tangential air inlet and an axial air outlet. The cyclone aerosolises and retains an aerosol of powdered medicament in an airflow circulating between the inlet and the outlet. The cyclone has an exit port which is open to atmosphere. When the aerosol is to be inhaled, the pressure in the cyclone is increased by increasing the airflow to the inlet which causes the aerosol to discharge through the exit port. The inhaler has the advantage that the rate of discharge of the aerosol can be controlled independently of the rate of airflow required to aerosolise the medicament.

What is claimed is:

1. An inhaler for producing an inhalable aerosol of a powdered medicament, the inhaler comprising:

an aerosolising device having an exit port and being arranged to retain, in use, an aerosol of a powdered medicament in a circulating airflow; and discharge means arranged to control the discharge of the aerosol through the exit port; wherein said aerosolising device has an inlet and an outlet and air is circulated by a pump from the outlet to the inlet in a recirculation loop.

2. An inhaler as claimed in claim 1, wherein, in use, the circulating airflow includes a rotating airflow in the aerosolising device.

3. An inhaler as claimed in any of claims 2, wherein the aerosolising device comprises a cyclone having a tangential inlet and an axial outlet.

4. An inhaler as claimed in claim 1, wherein the discharge means is arranged to provide a pressure differential across the exit port.

5. An inhaler as claimed in any of claims 4, wherein the discharge means is arranged to increase the pressure in the aerosolising device.

6. An inhaler as claimed in claim 5, wherein the discharge means is arranged to increase the airflow into the aerosolising device.

7. An inhaler as claimed in any of claims 4, wherein the discharge means is arranged to reduce the pressure on the side of the exit port remote from the aerosolising device.

8. An inhaler as claimed in claim 7, wherein the discharge means comprises a mouthpiece and, in use, inhalation by a user on the mouthpiece reduces the pressure on the side of the exit port remote from the aerosolising device.

9. An inhaler as claimed in claim 1, wherein, in use, the recirculation loop is closed while the aerosol is retained in the aerosolising device.

10. An inhaler as claimed in claim 1, wherein, in use, the exit port is open to atmosphere.

11. An inhaler for producing an inhalable aerosol of a powdered medicament, the inhaler comprising:

an aerosolising device having an inlet, an outlet and an exit port and being arranged to retain, in use, an aerosol of a powdered medicament in a circulating airflow; and discharge means arranged to control the discharge of the aerosol through the exit port; a chamber coupled to the inlet, the chamber arranged to receive a capsule of a medicament;

and a piercing device comprising a needle arranged to pass right through the capsule to form an entry hole and an exit hole therein, so that, in use, an airflow can pass through the capsule to entrain the medicament.

* * * * *

UNITED STATES PATENT AND TRADEMARK OFFICE
CERTIFICATE OF CORRECTION

PATENT NO. : 6,948,496 B2
DATED : September 27, 2005
INVENTOR(S) : Eason et al.

It is certified that error appears in the above-identified patent and that said Letters Patent is hereby corrected as shown below:

<u>Title page,</u>
Item [30], Foreign Application Priority Data, insert:
-- July 21, 2000        (GB)    Great Britain…………………….0018030.7 --.

Signed and Sealed this

Twenty-seventh Day of December, 2005

JON W. DUDAS
*Director of the United States Patent and Trademark Office*